United States Patent
Vockley et al.

(10) Patent No.: US 12,290,500 B2
(45) Date of Patent: May 6, 2025

(54) ANAPLEROTIC AGENTS FOR TREATMENT OF DISORDERS OF PROPIONATE AND LONG CHAIN FAT METABOLISM

(71) Applicant: University of Pittsburgh—Of the Commonwealth System of Higher Education, Pittsburgh, PA (US)

(72) Inventors: Gerard Vockley, Pittsburgh, PA (US); Al-Walid A. Mohsen, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 973 days.

(21) Appl. No.: 17/369,268

(22) Filed: Jul. 7, 2021

(65) Prior Publication Data
US 2021/0338624 A1    Nov. 4, 2021

Related U.S. Application Data

(62) Division of application No. 16/094,828, filed as application No. PCT/US2017/028100 on Apr. 18, 2017, now Pat. No. 11,083,702.

(60) Provisional application No. 62/324,537, filed on Apr. 19, 2016.

(51) Int. Cl.
| | |
|---|---|
| *A61K 31/225* | (2006.01) |
| *A61P 3/00* | (2006.01) |
| *C07C 69/40* | (2006.01) |
| *C07C 69/66* | (2006.01) |

(52) U.S. Cl.
CPC .............. *A61K 31/225* (2013.01); *A61P 3/00* (2018.01); *C07C 69/66* (2013.01)

(58) Field of Classification Search
CPC ...... A61K 31/225; C07C 69/66; C07C 69/67; C07C 69/40; A61P 3/00
See application file for complete search history.

(56) References Cited

U.S. PATENT DOCUMENTS

| | | |
|---|---|---|
| 9,416,364 B2 | 8/2016 | Gonzalez et al. |
| 10,035,819 B2 | 7/2018 | Evans et al. |
| 10,253,296 B2 | 4/2019 | Kahvejian et al. |
| 10,301,594 B1 | 5/2019 | Kahvejian et al. |
| 10,344,263 B2 | 7/2019 | Kahvejian et al. |
| 10,442,834 B2 | 10/2019 | Sajiki et al. |
| 10,525,029 B2 | 1/2020 | Jalan et al. |
| 2006/0241071 A1 | 10/2006 | Grinstaff et al. |
| 2012/0094293 A1 | 4/2012 | Spiegelman et al. |
| 2014/0343009 A1 | 11/2014 | Barth |
| 2015/0057363 A1 | 2/2015 | Miller et al. |
| 2015/0216824 A1 | 8/2015 | Mohamed et al. |
| 2020/0352894 A1* | 11/2020 | Levin ...................... C07C 69/40 |

FOREIGN PATENT DOCUMENTS

WO    WO-2014053857 A1 *    4/2014 ........... C07C 235/06

OTHER PUBLICATIONS

Ehinger et al. Nature communications 2016, 7, 12317, pp. 1-8.*
"Anaplerotic Therapy in Propionic Acidemia," NCT00645879, ClinicalTrials.gov, posted Mar. 28, 2008.
Baumgartner et al., "Proposed Guidelines for the Diagnosis and Management of Methylmalonic and Propionic Acidemia," *Orphanet J. Rare Dis.*, vol. 9:130-166, 2014.
Carrillo-Carrasco and Venditti, "Propionic Acidemia", GeneReviews®—NCBI Bookshelf, posted May 17, 2012.
Celato et al., "A new case of malonic aciduria with a presymptomatic diagnosis and an early treatment Succinic acid," *Brain & Development*, vol. 35:675-680, 2013.
Goetzman et al., "Long-chain Acyl-CoA Dehydrogenase Deficiency as a Cause of Pulmonary Surfactant Dysfunction," *J. Biol. Chem.*, vol. 289:10668-10679, 2014.
International Search Report and Written Opinion mailed on Jun. 28, 2017 for International Application No. PCT/US2017/028100 (12 pages).
Park et al., "Anaplerotic Triheptanoin Diet Enhances Mitochondrial Substrate Use to Remodel the Metabolome and Improve Lifespan, Motor Function, and Sociability in MeCP2-Null Mice," *PLoS One*, vol. 9:e109527, 2014.
Price, Leisa Bitner, "Anaplerotic Therapy in Propionic Acidemia," Thesis, College of Health, The University of Utah, May 2013.
† Roe & Brunengraber, "Anaplerotic treatment of long-chain fat oxidation disorders with triheptanoin: Review of 15 years Experience," *Mol Gen Metab.* 116, 260-268, 2015.
Shchelochkov et al. (NIH, US Library of Medicine, National Center of Biotechnology Information, Propionic Acidemia Gene u Reviews, Initial Posting: May 17, 2012; Last Update: Oct. 6, 2016).
Teja et al. (Accession No. 2017:1316180, Hcaplus, Document No. 167:273685, Fluvestrant formulations, Abstract of Patent No. IN2012CH01418).
Vockley et al., "Long-term Major Clinical Outcomes in Patients with Long Chain Fatty Acid Oxidation Disorders Before and After Transition to Triheptanoin Treatment—A Retrospective Chart Review," *Mol. Genet. Metab.*, vol. 116:53-60, 2015.

(Continued)

*Primary Examiner* — Irina Neagu

(74) *Attorney, Agent, or Firm* — Klarquist Sparkman, LLP

(57) ABSTRACT

Methods of treating propionic acidemia (PA), methylmalonic acidemia (MMA) and fatty acid oxidation disorders are described. The methods include administering an anaplerotic agent that can directly enter the tricarboxylic acid cycle, such as a succinate derivative or pro-drug, for example trisuccinylglycerol (TSG). Methods of restoring tricarboxylic acid (TCA) cycle function in a cell deficient for propionyl-CoA carboxylase (PCC) or methylmalonyl-CoA mutase (MUT) by contacting the cell with a succinate derivative or pro-drug, such as TSG, are also described.

10 Claims, 5 Drawing Sheets

(56) References Cited

OTHER PUBLICATIONS

Vockley, "Novel Therapies for Organic Acidemias", 2016 FOD/OAA International Metabolic Family Conference, Westminister, Colorado, Jul. 8-9, 2016, downloaded from http://www.oaanews.org/uploads/8/7/3/7/8737351 0/oafmilypresentation2016vockley.pdf.

Waisbren et al., "Neuropsychological Outcomes in Fatty Acid Oxidation Disorders: 85 Cases Detected by Newborn Screening," *Dev. Disabil. Res. Rev.*, vol. 17:260-268, 2013.

* cited by examiner

ANAPLEROTIC AGENTS FOR TREATMENT OF DISORDERS OF PROPIONATE AND LONG CHAIN FAT METABOLISM

CROSS REFERENCE TO RELATED APPLICATIONS

This is a divisional of U.S. application Ser. No. 16/094,828, filed Oct. 18, 2018, issued as U.S. Pat. No. 11,083,702 on Aug. 10, 2021, which is the U.S. National Stage of International Application No. PCT/US2017/028100, filed Apr. 18, 2017, published in English under PCT Article 21(2), which claims the benefit of U.S. Provisional Application No. 62/324,537, filed Apr. 19, 2016, which is herein incorporated by reference in its entirety.

ACKNOWLEDGMENT OF GOVERNMENT SUPPORT

This invention was made with government support under grant numbers FD003895 and DK078775 awarded by the National Institutes of Health. The government has certain rights in the invention.

FIELD

This disclosure concerns the treatment of disorders of propionate metabolism and long chain fatty acid oxidation by administration of anaplerotic agents that can directly enter the tricarboxylic acid cycle, such as trisuccinylglycerol or other succinate derivatives.

BACKGROUND

Methylmalonic and propionic acidemias (MMA/PA) are inborn errors of metabolism characterized by accumulation of propionic acid and/or methylmalonic acid due to deficiency of methylmalonyl-CoA mutase (MUT), methylmalonyl-CoA epimerase, succinyl-CoA synthetase (also known as ligase), or propionyl-CoA carboxylase (PCC). Deficiencies in MUT may be primary, due to mutations in this gene, or secondary, due to disorders of adenosylcobalamin synthesis. Patients present either shortly after birth with acute deterioration, metabolic acidosis and hyperammonemia, or later at any age with a more heterogeneous clinical picture, leading to early death or severe neurological handicap in many survivors. Mental outcome tends to be worse in PA and late complications include chronic kidney disease (particularly in MMA) and cardiomyopathy (primarily in PA). Except for vitamin $B_{12}$ responsive forms of MMA, the outcome remains poor despite the existence of effective therapy in the form of a low protein diet and carnitine. In the past, poor outcomes may have been related to under recognition and delayed diagnosis due to nonspecific clinical presentation and insufficient awareness of health care professionals in view of the rarity of the disease. However, these disorders are now diagnosed by newborn screening, offering the opportunity for early treatment and better outcome.

There is currently no specific medical therapy for disorders of propionate metabolism other than dietary restrictions. Carbaglu may improve ammonia metabolism in some patients, and liver transplantation is also an option in some cases. Triheptanoate, an anaplerotic agent, is currently in clinical trials for long chain fatty acid oxidation defects, but it cannot be used in short or medium chain disorders or in defects of propionate metabolism since propionyl-CoA is the end product of heptanoate metabolism. Thus, a need exists for an effective therapy for the treatment of propionate disorders.

SUMMARY

Methods of treating propionic acidemia (PA), methylmalonic acidemia (MMA) or a fatty acid oxidation disorder in a subject are provided. In some embodiments, the method includes administering to the subject a therapeutically effective amount of a succinate pro-drug, such as a compound of formula I or formula II. In some examples, the compound is trisuccinylglycerol (TSG).

Also provided are methods of restoring tricarboxylic acid (TCA) cycle function in a cell deficient for propionyl-CoA carboxylase (PCC) or methylmalonyl-CoA mutase (MUT). In some embodiments, the method includes contacting the cell with a succinate pro-drug, such as a compound of formula I or formula II, for example TSG. In some examples, the method is an in vitro method. In other examples, the method is an in vivo method and contacting the cell with the succinate pro-drug includes administering the succinate pro-drug to a subject with a PCC or MUT deficiency.

The foregoing and other objects, features, and advantages of the invention will become more apparent from the following detailed description, which proceeds with reference to the accompanying figures.

DETAILED DESCRIPTION

I. Abbreviations

BNP B-type natriuretic peptide
CPK creatine phosphokinase
FBS fetal bovine serum
HPLC high performance liquid chromatography
IP intraperitoneal
LC liquid chromatography
MCT medium chain triglyceride
MMA methylmalonic academia
MS mass spectrometry
MUT methylmalonyl-CoA mutase
PA propionic acidemia
PCC propionyl-CoA carboxylase
TCA tricarboxylic acid
TSG trisuccinylglycerol

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.),

*Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. a succinate pro-drug or derivative), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Alkyl: A saturated aliphatic hydrocarbyl group having from 1 to 25 carbon atoms, typically 1 to 10 carbon atoms such as 1 to 6 carbon atoms ($C_{1-6}$alkyl). This term includes, by way of example, linear and branched hydrocarbyl groups such as methyl ($CH_3$), ethyl (—$CH_2CH_3$), n-propyl (—$CH_2CH_2CH_3$), isopropyl (—$CH(CH_3)_2$), n-butyl (—$CH_2CH_2CH_2CH_3$), isobutyl (—$CH_2CH_2(CH_3)_2$), sec-butyl (—$CH(CH_3)(CH_2CH_3)$), t-butyl (—$C(CH_3)_3$), n-pentyl (—$CH_2CH_2CH_2CH_2CH_3$), and neopentyl (—$CH_2C(CH_3)_3$).

Anaplerotic agent: A substance that when incorporated into the TCA cycle either replenishes one or more depleted intermediates of the TCA cycle or maintains or increases the level of one or more intermediates of the TCA cycle, or both. The anaplerotic agents disclosed herein increase the level of succinate.

Contacting: Placement in direct physical association; includes both in solid and liquid form.

Figure 3:
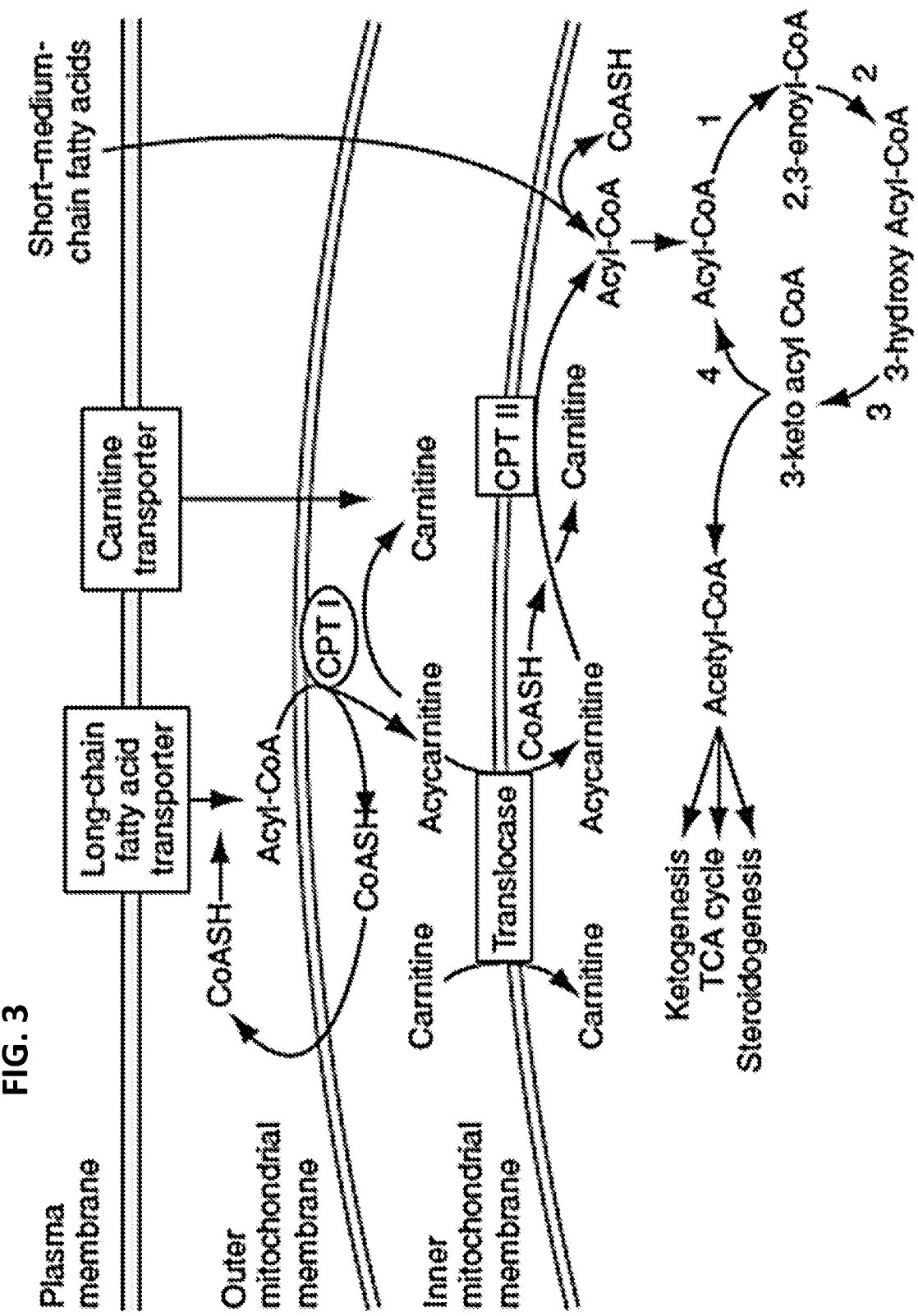
FIG. 3 is a schematic of the fatty acid metabolic pathway.
Figure 4:
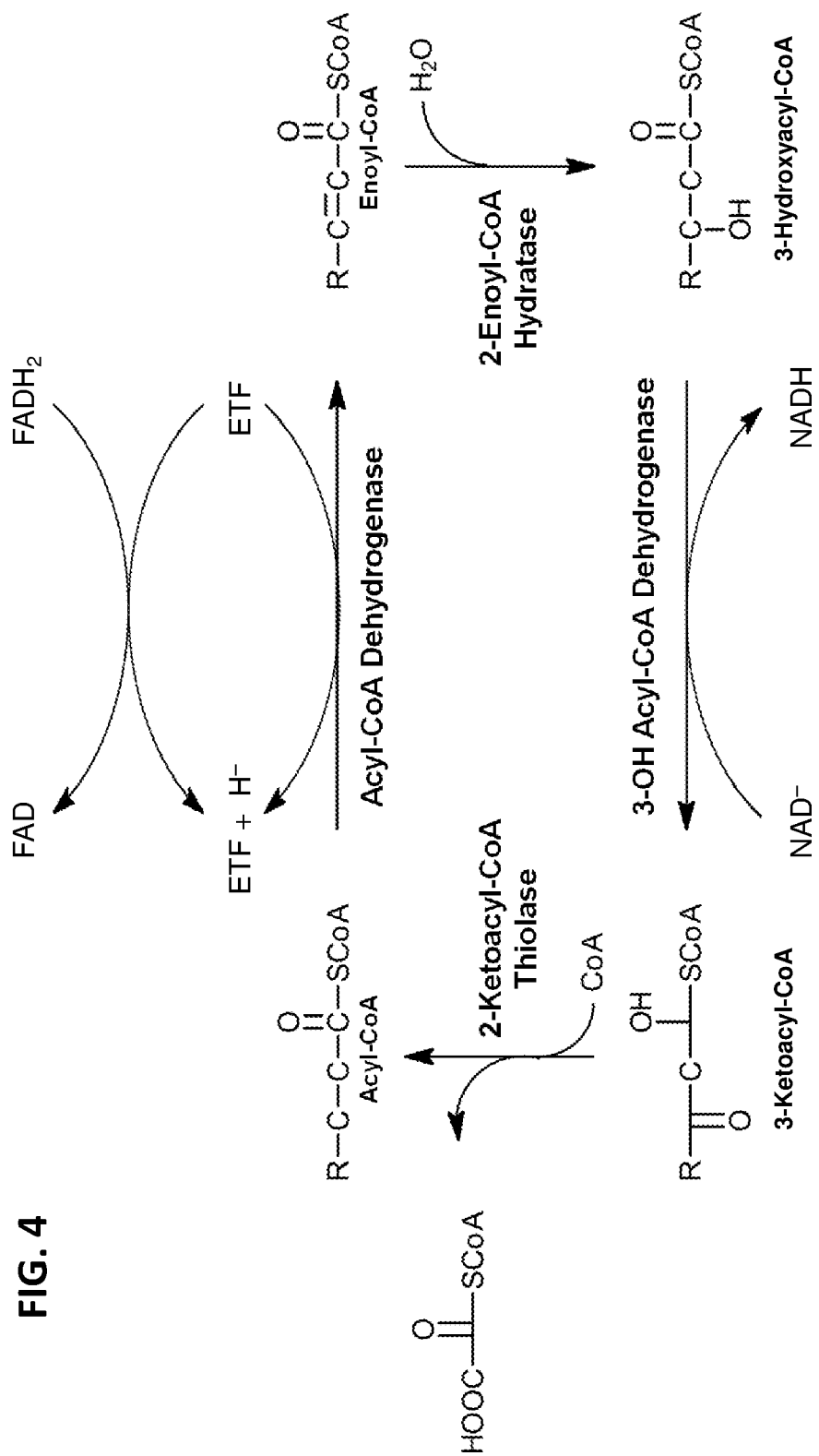
FIG. 4 is a schematic of fatty acid oxidation.

Fatty acid oxidation disorder: A group of inherited metabolic conditions that lead to an inability to metabolize fatty acids, and a decrease in cell energy metabolism. Each fatty acid oxidation disorder is associated with a specific enzyme defect in the fatty acid metabolic pathway and affects utilization of dietary and stored fat. At least 25 enzymes and specific transport proteins are responsible for carrying out the steps of mitochondrial fatty acid metabolism (see FIGS. 3 and 4; and Rinaldo et al., *Annu Rev Physiol* 64:477-502, 2002; Saudubray et al., *J Inherit Metab Dis* 29:261-274, 2006; Vockley and Whiteman, *Neuromuscul Disord* 12:235-246, 2002). Of these, defects in at least 22 have been shown to cause disease in humans (Vockley and Whiteman, *Neuromuscul Disord* 12:235-246, 2002).

Figure 1:
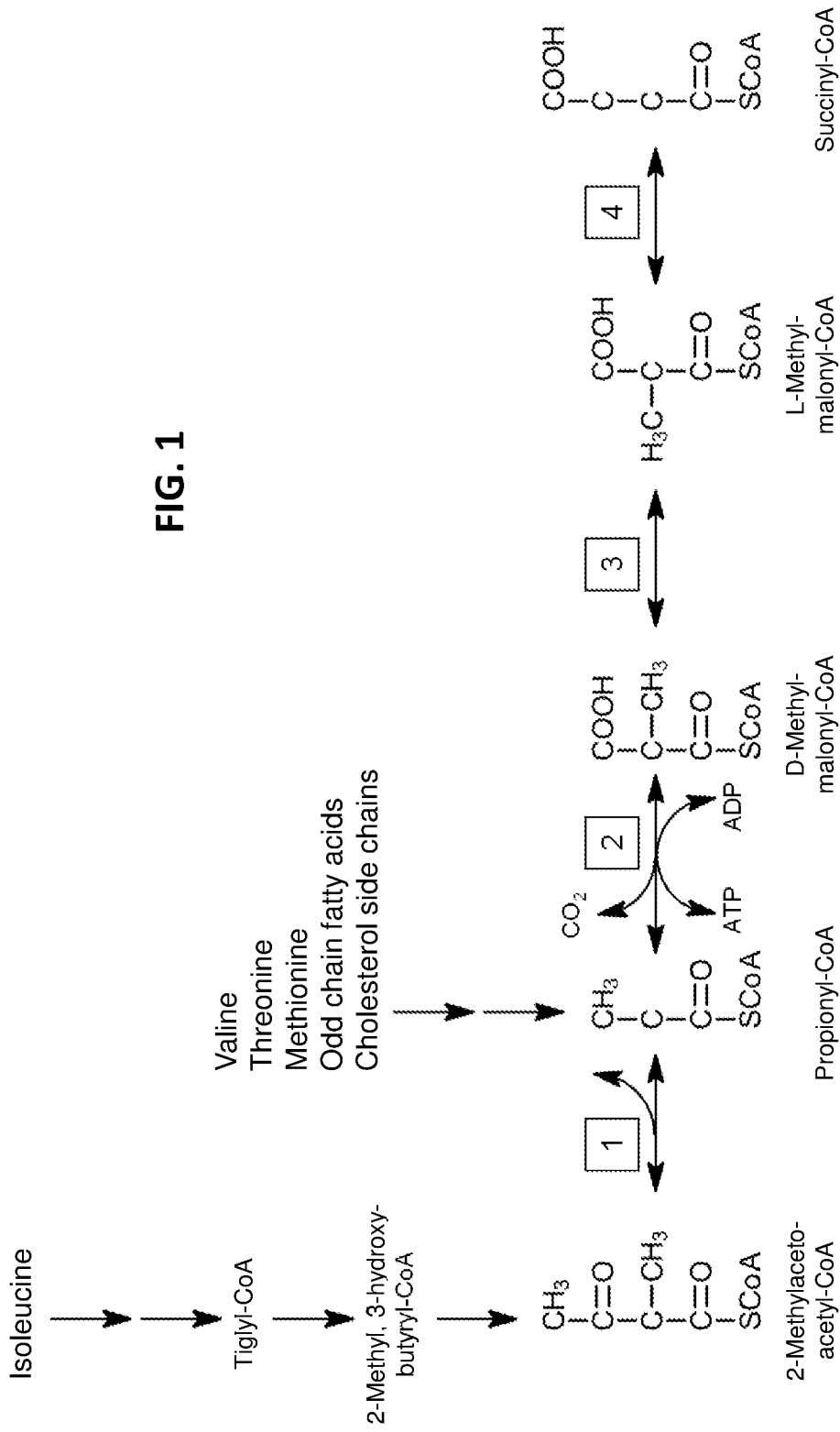
FIG. 1 is a schematic of the propionate metabolic pathway.
Figure 2:
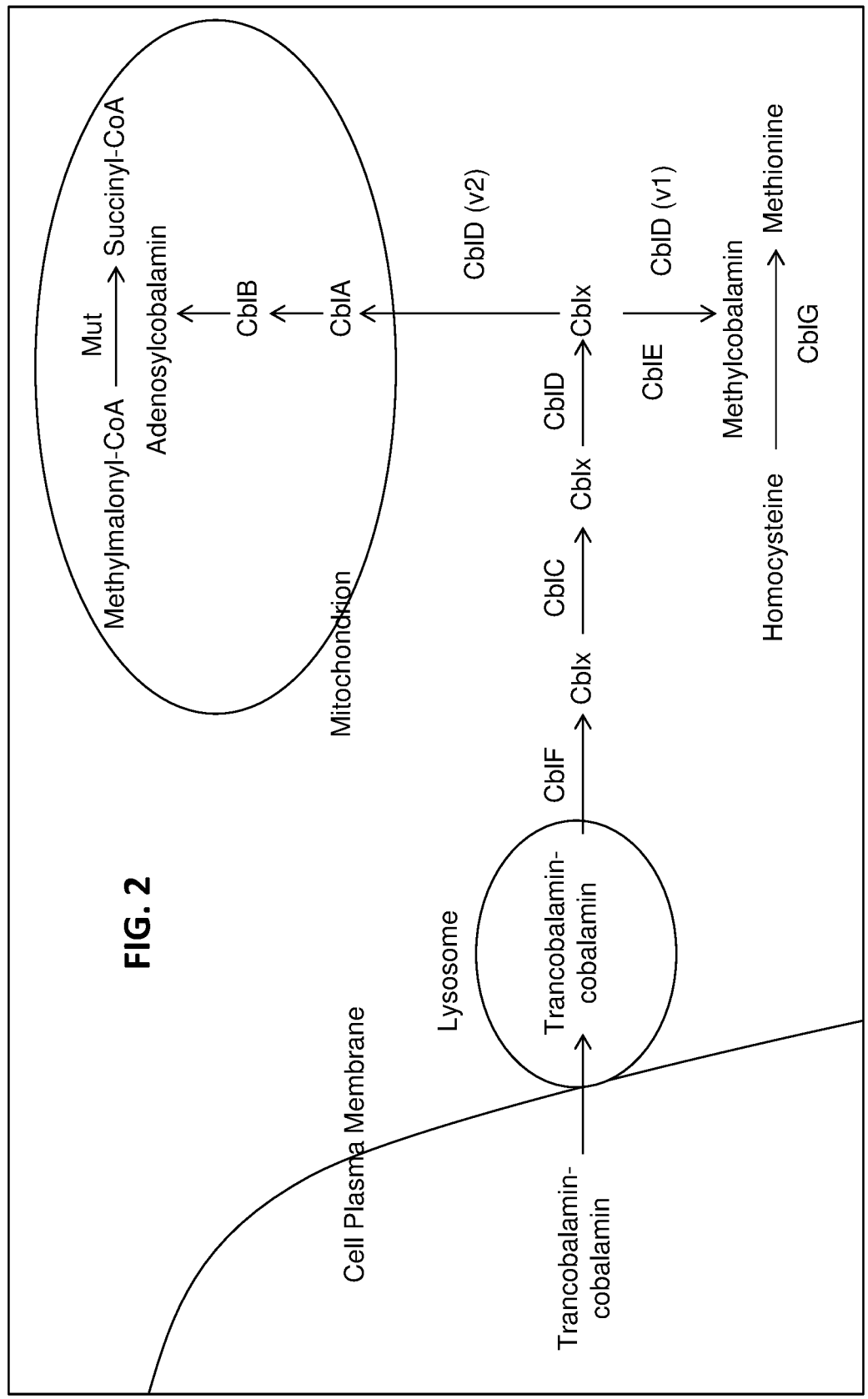
FIG. 2 is a schematic of the cobalamin metabolic pathway.

Methylmalonic acidemia (MMA): An autosomal recessive metabolic disorder. MMA is a classical type of organic acidemia. Patients with MMA are unable to properly digest specific fats and proteins, which in turn leads to buildup of a toxic level of methylmalonic acid in the blood. Inherited forms of MMA result from a deficiency of methylmalonyl-CoA mutase, an adenosylcobalamin-requiring enzyme that converts 1-methylmalonyl-CoA to succinyl-CoA (FIG. 1), or in the metabolic pathway that catalyzes the biosynthesis of adenosylcobalamin from vitamin B12 (FIG. 2).

Methylmalonyl-CoA mutase (MUT): An enzyme that catalyzes the isomerization of methylmalonyl-CoA to succinyl-CoA and is involved in key metabolic pathways. Deficiencies in MMA cause methylmalonic acidemia.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, PA, 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Pro-drug: A medication or compound that after administration is metabolized into a pharmacologically active compound or drug. In the context of the present disclosure, a succinate pro-drug is any compound that when administered to a subject is converted to succinate in the body. In some embodiments, the succinate pro-drug improves the bioavailability of succinate.

Propionic acidemia (PA): A rare, autosomal recessive metabolic disorder, classified as a branched-chain organic acidemia. PA is caused by mutations in propionyl-CoA carboxylase (PCC), a mitochondrial biotin-containing enzyme that catalyzes conversion of propionyl-CoA to D-methylmalonyl-CoA (FIG. 1). PA typically presents in the early neonatal period with progressive encephalopathy, though later onset forms exist. Death can occur quickly due to secondary hyperammonemia, infection, cardiomyopathy or basal ganglial stroke.

Propionyl-CoA carboxylase (PCC): A mitochondrial biotin-containing enzyme that catalyzes conversion of propionyl-CoA to D-methylmalonyl-CoA (see FIG. 1). A deficiency in PCC causes propionic acidemia.

Subject: Living multi-cellular vertebrate organisms, a category that includes human and non-human mammals.

Succinate: A TCA cycle intermediate. Succinate serves as an electron donor to the electron transport chain.

Succinate derivative: In the context of the present disclosure, a "succinate derivative" includes any derivative of succinate that could serve as an anaplerotic agent to restore succinate to the TCA cycle. In some embodiments, the succinate derivative is trisuccinylglycerol or trisuccinylglycerine.

Therapeutically effective amount: A quantity of a specified pharmaceutical or therapeutic agent (e.g. a succinate derivative such as TSG) sufficient to achieve a desired effect in a subject, or in a cell, being treated with the agent. The effective amount of the agent can be dependent on several factors, including, but not limited to the subject or cells being treated, and the manner of administration of the therapeutic composition.

Tricarboxylic acid (TCA) cycle: A series of chemical reactions used by all aerobic organisms to generate energy through the oxidation of acetyl-CoA derived from carbohydrates, fats and proteins into carbon dioxide and chemical energy in the form of adenosine triphosphate (ATP). The TCA cycle provides precursors of certain amino acids as well as the reducing agent NADH that is used in numerous other biochemical reactions. The TCA cycle is also known as the citric acid cycle or the Krebs cycle.

Figure 5:
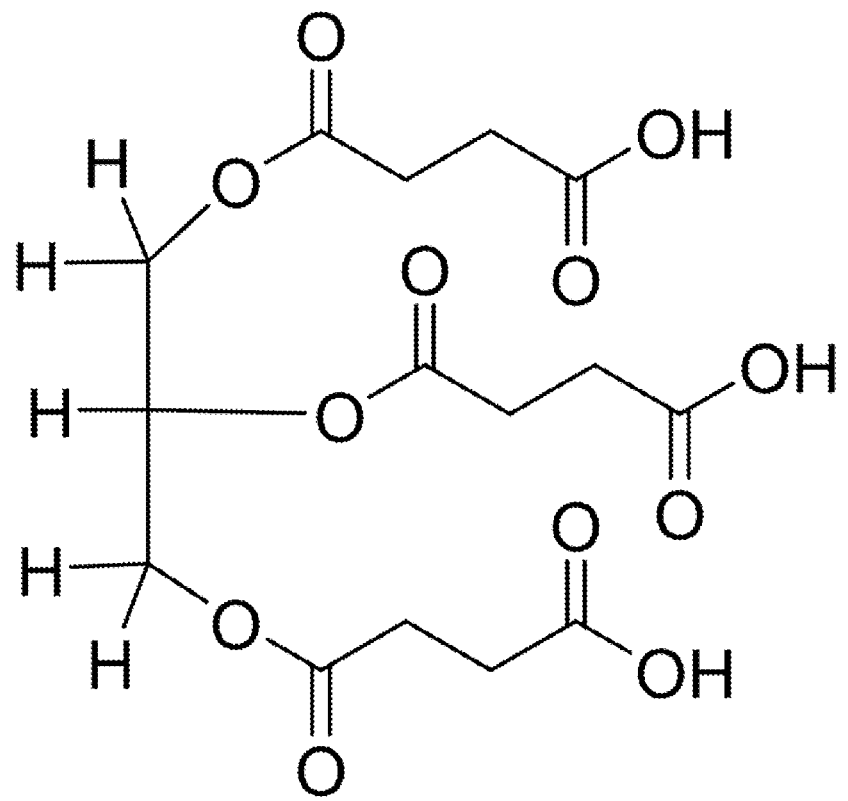
FIG. 5 shows the chemical structure of trisuccinylglycerol.

Trisuccinylglycerol (TSG): A triglycerol form of succinate. The IUPAC name of TSG is 4-[2,3-bis(3-carboxypropanoyloxy)propoxy]-4-oxobutanoic acid (CAS Registry Number: 10471-27-9). The chimerical structure of TSG is shown in FIG. 5. Synonyms of TSG include, for example, UNII-80CAB03D7S, glyceroltrisuccinat, glycerintrisuccinate, glycerinetrisuccinate, glycerin trisuccinate, glycerintrisuccinate, glycerol trisuccinate, glyceryl trisuccinate, AGN-PC-0A97MT, 80CAB03D7S, SCHEMBL1405394, succinic acid, 1,2,3-propanetriyl ester, butanedioic acid, 1,1',1"-(1,2,3-propanetriyl) ester, and 4-[2,3-bis(3-carboxypropanoyloxy)propoxy]-4-oxobutanoic acid.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

It has been demonstrated that secondary deficiency of the tricarboxylic acid (TCA) cycle is a common cause of symptoms (including cardiomyopathy) in patients with fatty acid oxidation defects, and that it can successfully be treated through an anaplerotic medication that provides succinate to the TCA cycle in the form of propionyl-CoA (Vockley et al., *Mol Genet Metab* 116:53-60, 2015). It is believed that cardiomyopathy in propionic acidemia is similarly due to a secondary defect in the TCA cycle and would respond to treatment with anaplerotic agents. However, the existing anaplerotic therapy cannot be used to treat PA. Thus, it is contemplated herein to use trisuccinylglycerol, or other pro-drugs of succinate, for treatment of disorders of propionate and long chain fatty acid oxidation disorders. Specifically, this therapy can be used to treat genetic defects in propionic acidemia, the next two steps in the metabolism of propionate, methylmalonic acidemia (MMA) and succinyl-CoA lyase. It also provides an alternative to triheptanoin for anaplerotic therapy in fatty acid oxidation defects. In total, the incidence of these defects is ~1:10,000-20,000 live births.

Succinate is a TCA cycle intermediate that has been used clinically in the treatment of mitochondrial oxidative phosphorylation deficiencies. While it is suitable for in vitro experiments in cells, it is difficult to deliver pharmacologically relevant doses in patients. The use of a triglycerol form of succinate, trisuccinylglycerol (TSG), to reverse TCA cycle deficits is disclosed herein. Other derivatives and/or pro-drugs of succinate, and other TCA cycle intermediates or their derivatives may also be used, such as a compound of formula I or formula II disclosed herein.

IV. Overview of Several Embodiments

Methods of treating propionic acidemia (PA), methylmalonic acidemia (MMA) or a fatty acid oxidation disorder in a subject are disclosed herein. The methods include administering to the subject a therapeutically effective amount of an anaplerotic agent, such as a succinate derivative or pro-drug, for example a compound of formula I or formula II disclosed herein.

Provided herein is a method of treating PA, MMA or a fatty acid oxidation disorder in a subject by administering to the subject a therapeutically effective amount of a compound of formula I

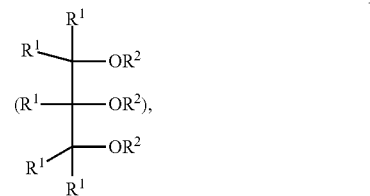

or a pharmaceutically acceptable salt or hydrate thereof, wherein each $R^1$ independently is H or alkyl; each $R^2$ independently is succinate, malate, fumarate, citrate, D-isocitrate, cis-aconitate or alpha-ketoglutarate; and n is from 0 to 6.

In some embodiments, each $R^1$ independently is H, or $C_{1-6}$alkyl, such as methyl, ethyl, propyl, butyl, pentyl, hexyl, or a stereo and/or position isomer thereof. In particular embodiments, each $R^1$ independently is methyl, ethyl, n-propyl or isopropyl. In specific non-limiting examples, each $R^1$ is H.

In some embodiments, each $R^2$ independently has a structure selected from

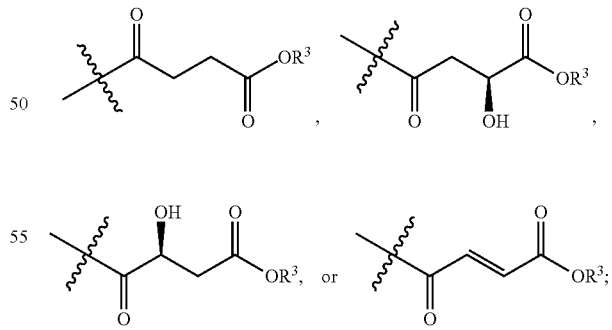

where the wavy line " $\sim\!\sim\!\sim$ " indicates the point of attachment of each $R^2$ moiety to the parent structure, and each $R^3$ independently is H or $C_{1-6}$alkyl, such as methyl, ethyl, propyl, butyl, pentyl, hexyl, or a stereo and/or positional isomer thereof. In particular embodiments, each $R^3$ independently is H, methyl, ethyl, n-propyl or isopropyl. In specific non-limiting embodiments, each $R^3$ is H.

In some embodiments, each $R^2$ is

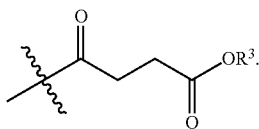

In particular examples, each $R^2$ is succinate.

In some embodiments, n is from 1 to 4. In particular embodiments, n is 1 or 2.

In particular non-limiting examples, n is 1.

In specific examples, the compound is trisuccinylglycerol. In some examples, trisuccinylglycerol is administered to the subject once per day.

In some embodiments, the compound is administered orally or intravenously. In some examples, the compound is administered once a day. In other examples, the compound is administered in multiple divided doses.

Also provided herein is a method of treating PA, MMA or a fatty acid oxidation disorder in a subject by administering to the subject a therapeutically effective amount of a compound of formula II

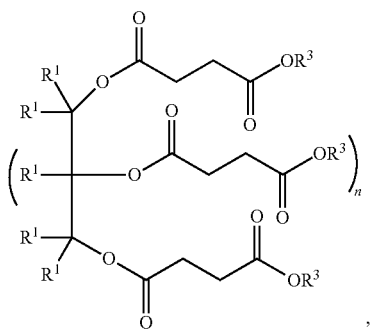

or a pharmaceutically acceptable salt or hydrate thereof, wherein each $R^1$ independently is H or alkyl; each $R^3$ independently is H or $C_{1-6}$alkyl; and n is from 0 to 6.

In some embodiments, each $R^1$ is H.

In some embodiments, each $R^3$ is H.

In some embodiments, n is from 1 to 4. In particular embodiments, n is 1 or 2.

In particular non-limiting examples, n is 1.

In specific examples, the compound is trisuccinylglycerol. In some examples, trisuccinylglycerol is administered to the subject once per day.

In some embodiments, the compound is administered orally or intravenously. In some examples, the compound is administered once a day. In other examples, the compound is administered in multiple divided doses.

In some embodiments of the methods described above, the method further includes selecting a subject diagnosed with PA and administering to the subject a therapeutically effective amount of the compound.

In some embodiments of the methods described above, the method further includes selecting a subject diagnosed with MMA and administering to the subject a therapeutically effective amount of the compound.

In some embodiments of the methods described above, the method further includes selecting a subject diagnosed with the fatty acid oxidation disorder and administering to the subject a therapeutically effective amount of the compound.

Methods of restoring tricarboxylic acid (TCA) cycle function in a cell deficient for propionyl-CoA carboxylase (PCC) or methylmalonyl-CoA mutase (MUT) are disclosed herein. The methods include contacting the cell with an anaplerotic agent, such as a succinate derivative or pro-drug, for example a compound of formula I or formula II disclosed herein.

Provided herein is a method of restoring TCA cycle function in a cell deficient for PCC or MUT by contacting the cell with a compound of formula I

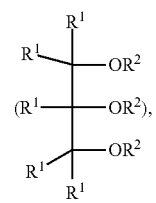

or a pharmaceutically acceptable salt or hydrate thereof, wherein each $R^1$ independently is H or alkyl; each $R^2$ independently is succinate, malate, fumarate, citrate, D-isocitrate, cis-aconitate or alpha-ketoglutarate; and n is from 0 to 6.

In some embodiments, each $R^1$ independently is H, or $C_{1-6}$alkyl, such as methyl, ethyl, propyl, butyl, pentyl, hexyl, or a stereo and/or position isomer thereof. In particular embodiments, each $R^1$ independently is methyl, ethyl, n-propyl or isopropyl. In specific non-limiting examples, each $R^1$ is H.

In some embodiments, each $R^2$ independently has a structure selected from

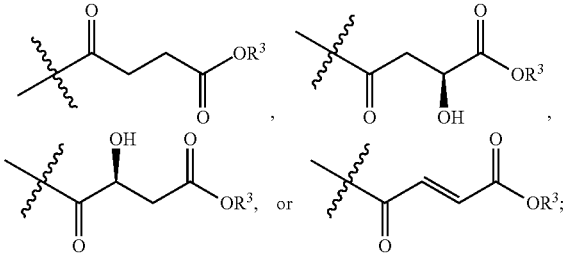

where the wavy line "〜" indicates the point of attachment of each $R^2$ moiety to the parent structure, and each $R^3$ independently is H or $C_{1-6}$alkyl, such as methyl, ethyl, propyl, butyl, pentyl, hexyl, or a stereo and/or positional isomer thereof. In particular embodiments, each $R^3$ independently is H, methyl, ethyl, n-propyl or isopropyl. In specific non-limiting embodiments, each $R^3$ is H.

In some embodiments, each $R^2$ is

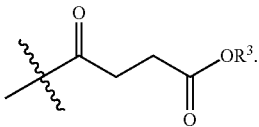

In particular examples, each $R^2$ is succinate.

In some embodiments, n is from 1 to 4. In particular embodiments, n is 1 or 2. In particular non-limiting examples, n is 1.

In specific examples, the compound is trisuccinylglycerol. In some examples, trisuccinylglycerol is administered to the subject once per day.

In some embodiments, the compound is administered orally or intravenously. In some examples, the compound is administered once a day. In other examples, the compound is administered in multiple divided doses.

Further provided is a method of restoring TCA cycle function in a cell deficient for PCC or MUT by contacting the cell with a compound of formula II

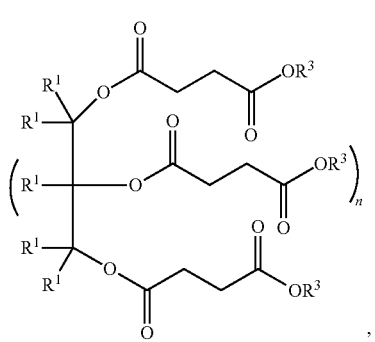

or a pharmaceutically acceptable salt or hydrate thereof, wherein each $R^1$ independently is H or alkyl; each $R^3$ independently is H or $C_{1-6}$alkyl; and n is from 0 to 6.

In some embodiments, each $R^1$ is H.

In some embodiments, each $R^3$ is H.

In some embodiments, n is from 1 to 4. In particular embodiments, n is 1 or 2.

In particular non-limiting examples, n is 1.

In specific examples, the compound is trisuccinylglycerol. In some examples, trisuccinylglycerol is administered to the subject once per day.

In some embodiments, the compound is administered orally or intravenously. In some examples, the compound is administered once a day. In other examples, the compound is administered in multiple divided doses.

In some embodiments of the methods of restoring TCA cycle function in a cell deficient for PCC or MUT, the method is an in vitro method. In other embodiments, the method is an in vivo method and contacting the cell with the compound comprises administering the compound to a subject with a PCC or MUT deficiency. In some examples, trisuccinylglycerol is administered to the subject once per day.

V. Disorders of Propionate and Long Chain Fat Metabolism

A. Propionic Acidemia (PA)

Propionic acidemia (PA) is one of the more common organic acidemias; it was first described in 1968 in an infant with severe metabolic acidosis. Propionyl-CoA is an intermediate in the oxidation of four amino acids (i.e., threonine, valine, methionine and isoleucine) as well as odd-chain fatty acids. PA is caused by mutations in propionyl-CoA carboxylase (PCC), a mitochondrial biotin-containing enzyme that catalyzes conversion of propionyl-CoA to D-methylmalonyl-CoA (FIG. 1). Propionate is a key precursor of the tricarboxylic acid (TCA) cycle metabolite succinate (propionyl-CoA methylmalonyl-CoA succinyl-CoA succinate). PA is extremely variable and identification through newborn screening is possible. The disorder may present in the first week of life with feeding difficulties, lethargy, vomiting, and life-threatening acidosis, hypoglycemia, hyperammonemia, and bone marrow suppression. Mortality in early onset disease is high, leading to its inclusion in all newborn screening programs in the U.S. Equally common is a more chronic course, which presents in the first months of life with poor feeding and episodes of vomiting, infection-induced ketoacidosis, failure to thrive, and osteoporosis severe enough to cause pathologic fractures. Developmental retardation, which is probably due to neonatal hyperammonemia or chronic illness, is common, and metabolic strokes due to acute degeneration of the basal ganglia may occur during or between episodes of ketoacidosis. Pancreatitis is an increasingly recognized complication of the disease. Cardiomyopathy, which may be rapidly fatal, occurs frequently and does not respond to carnitine. Adult onset disease with isolated cardiomyopathy has been reported.

1. Clinical Course

PA may present in the first week of life with feeding difficulties, lethargy, vomiting, and life-threatening acidosis, hypoglycemia, hyperammonemia, and bone marrow suppression (Shafai et al., *J Pediatr* 92:84-86, 1978; Wadlington et al., *J Pediatr* 86:707-712, 1975). Severe hyperammonemia likely contributes appreciably to the encephalopathy of the acutely ill neonate, possibly because propionyl-CoA inhibits the synthesis of N-acetylglutamate, the major allosteric activator of carbamyl phosphate synthetase. Mortality in early onset disease is high (Sass et al., *Clin Pediatr (Phila)* 43:837-843, 2004). Equally common is a more chronic course, which presents in the first months of life with poor feeding and episodes of vomiting, infection-induced ketoacidosis, failure to thrive, and osteoporosis severe enough to cause pathologic fractures. Developmental retardation, which is probably due to neonatal hyperammonemia or chronic illness, is common, and metabolic strokes due to acute degeneration of the basal ganglia may occur during or between episodes of ketoacidosis (Surtees et al., *Pediatr Neurol* 8:333-337, 1992). Cardiomyopathy, which may be rapidly fatal, occurs frequently and does not respond to carnitine (Massoud and Leonard, *Eur J Pediatr* 152:441-445, 1993). Adult onset disease with isolated cardiomyopathy has been reported. Pancreatitis is an increasingly recognized complication of the disease (Bultron et al., *J Pediatr Gastroenterol Nutr* 47:370-371, 2008). Before expanded newborn screening, most patients did not survive beyond the first decade of life, with death often occurring during an episode of ketoacidosis in a chronically malnourished child. Newborn screening via tandem mass spectroscopy reliably can identify propionic academia before symptoms occur and a much milder clinical spectrum results. However, the specificity of moderately elevated C3 carnitine levels in newborns remains controversial.

A common mutation in Plain Communities (Amish and Mennonite) is a frequent cause of adolescent and adult onset cardiomyopathy and sudden death in this population, but its pathophysiology remains unknown. The common PCC mutation in this population was previously felt to be a relatively mild condition. However, it is now clear that at least ⅓ of the Amish/Mennonites with PA develop cardiomyopathy, and sudden death as adults may be their presenting sign.

2. Diagnosis

Urine organic acids at diagnosis show large amounts of 3-hydroxypropionic and methylcitric acids, often with propionylglycine and tiglylglycine, and abnormal ketone bodies such as 3-hydroxy-n-valeric and 3-keto-n-valeric acids. Acylcarnitine analysis by tandem mass spectrometer shows increased C3 carnitine, and glycine levels are often elevated in blood and urine. Although usually not necessary, the enzyme defect can be demonstrated in many tissues, including leukocytes and cultured fibroblasts. Molecular testing is clinically available. Prenatal diagnosis has been accomplished with metabolite, enzymatic, and molecular techniques (Perez-Cerda et al., *Prenat Diagn* 24:962-964, 2004).

3. Treatment

Acute therapy is directed to treating shock, acidosis, hypoglycemia, and hyperammonemia with fluids, bicarbonate, glucose, and dialysis. Restriction of dietary natural protein (or of propiogenic amino acids) to amounts necessary to support normal growth and development is indicated, and usually results in natural protein intake less than 1 g/kg/day. Specialized formula restricted in isoleucine, valine, methionine, and threonine is used to provide additional protein for growth. Biotin supplementation is not clinically useful, but oral carnitine may be helpful to increase excretion of non-toxic metabolites. N-carbamylglutamate may help resolve hyperammonemia more quickly in some patients during episodes of acute metabolic decompensation (Tuchman et al., *Pediatr Res* 64:213-217, 2008; Mew et al., *Pediatrics* 126:e208-e214, 2010). Metronidazole given on an intermittent basis decreases the load of propiogenic bacteria in the bowel. Liver transplant reduces, but does not eliminate the risk for episodes of metabolic decompensation and can reverse cardiomyopathy in some patients (Saudubray et al., *Eur J Pediatr* 158(Suppl 2):S65-S69, 1999; Romano et al., *J Pediatr* 156:128-34, 2010).

B. Methylmalonic Acidemia

Methylmalonic acidemia can be caused by an inherited deficiency of methylmalonyl-CoA mutase, an adenosylcobalamin-requiring enzyme that converts 1-methylmalonyl-CoA to succinyl-CoA (FIG. 1), or in the metabolic pathway that catalyzes the biosynthesis of adenosylcobalamin from vitamin B12 (FIG. 2). When the latter defect occurs in a proximal step that also impairs the synthesis of methylcobalamin, homocysteine accumulates behind a block in N5-methyltetrahydrofolate: homocysteine methyltransferase. Recently, a defect in the methylmalonyl-CoA epimerase has been described (FIG. 1). Deficiency of succinyl-CoA synthetase results in methylmalonic acidemia with lactic acidosis.

1. Clinical Course

The clinical course of the disorders leading to methylmalonic acidemia vary considerably depending on the precise metabolic defect (Deodato et al., *Am J Med Genet C Semin Med Genet* 142C:104-112, 2006). The clinical presentation, course, and postmortem findings of complete methylmalonyl-CoA mutase deficiency mimic those of propionic acidemia. Many present with severe ketoacidosis, hyperammonemia, and thrombocytopenia in the first days or weeks of life. Acute striatal degeneration is a frequent complication of the disease, and late-developing interstitial nephritis and renal failure are common. Patients with later onset forms due to some residual mutase activity manifest a variety of symptoms, including intermittent ataxia, recurrent vomiting, failure to thrive, and developmental delay. In either setting, life threatening episodes of decompensation are typically due to minor intercurrent illnesses. Patients with cblA and cblB defects usually have isolated methylmalonic acidemia and somewhat milder disease. Secondary respiratory chain deficiencies have been reported with several of the disorders of methylmalonyl-CoA metabolism (de Keyzer et al., *Pediatr Res* 66:91-95, 2009; Valayannopoulos et al., *J Inherit Metab Dis* 32:159-162, 2009).

Methylmalonyl-CoA epimerase catalyzes the interconversion of D- and L-methylmalonyl-CoA and its deficiency results in a mild phenotype with isolated methylmalonic acidemia (Bikker et al., *Hum Mutat* 27:640-643, 2006). Mutations in the SUCLA2 gene, which encodes an ATP forming subunit of the Krebs cycle enzyme succinyl-CoA synthase, is a novel cause of methylmalonic acidemia. Affected patients have a severe phenotype including hypotonia, muscle atrophy, hyperkinesia, mental retardation, growth failure, central and cortical atrophy of the brain, and basal ganglia atrophy (Ostergaard et al., *Brain* 130:853-861, 2007).

Mutations in the CblC gene cause combined methylmalonic acidemia and homocystinemia. CblC deficiency most commonly presents in infancy with severe clinical manifestations including basal ganglia necrosis, microcephaly, failure to thrive, mental retardation, retinopathy, and megaloblastic anemia. Thromboembolic events can occur due to elevated homocysteine in blood. However, patients with milder, late onset disease have been reported (Morel et al., *Mol Genet Metab* 88:315-321, 2006). CblD mutations can cause combined disease as seen in CblC deficient patients, but variants with isolated methylmalonic acidemia as well as isolated homocystinemia have been identified (Miousse et al., *J Pediatr* 154:551-556, 2009). Patients with defects in the CblE and CblG groups are deficient only in methylcobalamin biosynthesis, and have homocystinuria without methylmalonic aciduria (Watkins and Rosenblatt, *Am J Med Genet* 34:427-434, 1989). CblF deficiency results in defective transport of B12 out of lysosomes and a combined methylmalonic acidemia and homocystinemia (Rutsch et al., *Nat Genet* 41:234-239, 2009). The clinical picture can be severe or mild. Methylmalonic acidemia is now often identified through newborn screening by tandem mass spectrometry, however, reports of the clinical efficacy of early detection have been mixed (Deodato et al., *Am J Med Genet C Semin Med Genet* 142C:104-112, 2006; Sniderman et al., *J Pediatr* 134:675-80, 1999; Leonard et al., *Eur J Pediatr* 162:S21-S24, 2003).

2. Diagnosis

Urine organic acids show increased methylmalonic acid and, especially in mutase deficient patients, 3-hydroxypropionic and methylcitric acids, and tiglylglycine (Deodato et al., *Am J Med Genet C Semin Med Genet* 142C:104-112, 2006). The same abnormal ketone bodies noted in propionic acidemia are observed in this condition. Acylcarnitine analysis by tandem mass spectrometry shows increased C3 carnitine, and glycine is usually elevated in blood and urine. Megaloblastosis is often observed in patients with the cblC, cblD, and cblF defects. The homocystinemia and homocystinuria seen in such patients is accompanied by low methionine and high cystathionine in serum and not, as in cystathionine synthetase deficiency, by high methionine and low cystathionine. Excretion of methylmalonic acid can be seen in dietary B12 deficiency but is not as pronounced as in the inherited disorders unless the vitamin deficiency is very severe (Higginbottom et al., *N Engl J Med* 299:317-323, 1978). Differentiation among the various enzyme deficiencies often requires a combination of fibroblast enzyme analysis, complementation studies, and molecular sequencing of candidate genes.

3. Treatment

As in propionic acidemia, treatment in episodes of acute metabolic decompensation is directed first to treating shock, acidosis, hypoglycemia, and hyperammonemia, followed by restriction of protein (specifically, propiogenic amino acids). Carnitine is used to treat secondary carnitine deficiency. Some patients treated in this manner do well, but many do not and die in early childhood, often during an episode of ketoacidosis (Deodato et al., *Am J Med Genet C Semin Med Genet* 142C:104-112, 2006). Patients with defects in cobalamin metabolism may respond partially or completely to supplementation with intramuscular hydroxycobalamin, but residual metabolic abnormalities are common. Betaine hydrochloride, which promotes conversion of homocysteine to methionine by betaine:homocysteine methyltransferase, can decrease homocystine levels in blood in patients with combined disorders. Liver transplantation can be curative, and one patient with chronic renal failure was treated successfully with combined liver-kidney transplantation (Meyburg and Hoffmann, Transplantation 80:S135-S137, 2005; van't Hoff et al., *J Pediatr* 132:1043-1044, 1998).

Patients with defects in adenosyl-B12 biosynthesis often respond to large doses of B12. Even with treatment, however, many patients succumb to pancytopenia, renal involvement and neurologic impairment resembling hemolytic-uremic syndrome or to metabolic coma and cardiorespiratory arrest during childhood. Long-term survival does, however, occur, often with neurologic deficits. Prenatal diagnosis by metabolite, enzyme, or molecular analysis should be possible for all of the disorders.

C. Fatty Acid Oxidation Disorders

Mitochondrial fatty acid oxidation is a complex process involving transport of activated acyl-CoA moieties into the mitochondria, and sequential removal of 2 carbon acetyl-CoA units. It is the main source of energy for many tissues including heart and skeletal muscle and is critically important during times of fasting or physiologic stress. When the body's glycogen stores are depleted, long-chain fatty acids are mobilized from adipose tissue and taken up by liver and muscle cells. While short- and medium-chain fatty acids (C4 to C12) diffuse freely across plasma and mitochondrial membranes, the transport of longer chain species (C14 to C20) depends at least in part on active transport, a high-affinity mechanism of major physiological importance in skeletal muscle, liver, and adipocytes (Schaffer, *Am J Physiol Endocrinol Metab* 282:E239-E246, 2002; Stump et al., *J Lipid Res* 42:509-520, 2001).

Two additional enzymatic steps are necessary for the complete oxidation of mono- and di-unsaturated fatty acids, 2,4 dienoyl-CoA reductase and an enoyl-CoA isomerase, which allow for the complete oxidation of physiologically abundant fatty acids such as linoleate (C18:2) and oleate (C18:1) (Helander et al., *Genomics* 46:112-119, 1997; Miinalainen et al., *PLoS Genet* 5:e1000543, 2009). Each cycle of the pathway produces a molecule of acetyl-CoA and a fatty acid with two fewer carbons. Under physiological conditions, the latter re-enters the cycle until it is completely consumed. In peripheral tissues, the acetyl-CoA is terminally oxidized in the Krebs cycle for ATP production. In the liver, the acetyl-CoA from fatty acid oxidation can instead be utilized for the synthesis of ketones, 3-hydroxybutyrate, and acetoacetate, which are then exported for final oxidation by brain and other tissues (Fukao et al., *Pediatr Res* 42:498-502, 1997). At least 25 enzymes and specific transport proteins are responsible for carrying out the steps of mitochondrial fatty acid metabolism, some of which have only recently been recognized (FIGS. 3 and 4) (Rinaldo et al., *Annu Rev Physiol* 64:477-502, 2002; Saudubray et al., *J Inherit Metab Dis* 29:261-274, 2006; Vockley and Whiteman, *Neuromuscul Disord* 12:235-246, 2002). Of these, defects in at least 22 have been shown to cause disease in humans (Vockley and Whiteman, *Neuromuscul Disord* 12:235-246, 2002).

Most patients with fatty acid oxidation defects are now identified through newborn screening by tandem mass spectrometry of carnitine esters in blood spots. Unscreened patients can present throughout life. In the first week of life, cardiac arrhythmias, hypoglycemia, sudden death, and occasionally facial dysmorphism and malformations, including renal cystic dysplasia are seen.

Symptoms later in infancy and early childhood may relate to the liver or cardiac or skeletal muscle dysfunction, and include fasting or stress-related hypoketotic hypoglycemia or Reye-like syndrome, conduction abnormalities, arrhythmias or dilated or hypertrophic cardiomyopathy, and muscle weakness or fasting- and exercise-induced rhabdomyolysis. Adolescent or adult onset muscular symptoms, including rhabdomyolysis, and cardiomyopathy predominate. Diagnosis can usually be established even when the patient is asymptomatic, though analysis of samples during acute illness can uncover some mild cases. The most important single diagnostic test is analysis of acylcarnitine esters in serum, plasma, or dried blood spots by tandem MS, which will identify characteristic compounds in many of these conditions. Other tests that may be useful include urine organic acids and acylglycines, free and total carnitine in serum and urine, and enzyme assays or flux studies in leukocytes or fibroblasts. Treatment of the acute encephalopathy of hypoketotic hypoglycemia is by intravenous glucose and L-carnitine. Long-term therapy involves replenishing carnitine stores with L-carnitine, and preventing hypoglycemia. In some cases this can be done by providing a snack, glucose polymers, or uncooked cornstarch before bedtime, but in others requires continuous intragastric feeding. Supplementation with medium chain triglyceride (MCT) oil provides a fat source that can be utilized by patients with long chain defects, but is toxic to those with medium or short chain disorders.

VI. Trisuccinylglycerol and Other Succinate Pro-Drugs

Methods of treating organic acidemias and fatty acid oxidation disorders by administering a compound that functions as a pro-drug of succinate are disclosed herein.

In some embodiments, the compound comprises formula I

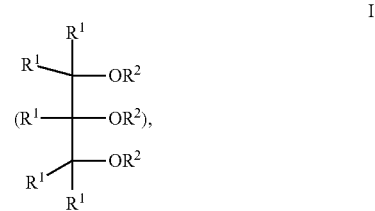

or a pharmaceutically acceptable salt or hydrate, thereof. With respect to formula I, each $R^1$ independently is H or alkyl; each $R^2$ independently is succinate, malate, fumarate, citrate, D-isocitrate, cis-aconitate or alpha-ketoglutarate; and n is from 0 to 6, such as 0, 1, 2, 3, 4, 5, or 6. In some embodiments, n is from 1 to 4, such as from 1 to 2, and in particular non-limiting embodiments, n is 1.

Each $R^1$ independently may be H, or $C_{1-6}$alkyl, such as methyl, ethyl, propyl, butyl, pentyl, hexyl, or stereo and/or position isomers thereof. In some embodiments, each $R^1$ independently is methyl, ethyl, n-propyl or isopropyl, and in certain embodiments, each $R^1$ is H.

In some embodiments, each $R^2$ independently has a structure selected from

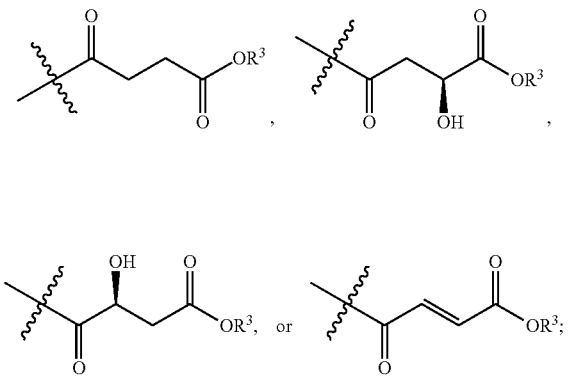

where the wavy line "〰" indicates the point of attachment of each $R^2$ moiety to the parent structure, and each $R^3$ independently is H or $C_{1-6}$alkyl, such as methyl, ethyl, propyl, butyl, pentyl, hexyl, or a stereo and/or positional isomer thereof. In some embodiments, each $R^3$ independently is H, methyl, ethyl, n-propyl or isopropyl, and in certain embodiments, each $R^3$ is H.

In some embodiments, each $R^2$ is

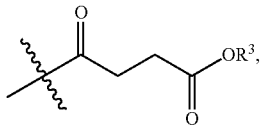

leading to compounds having formula II

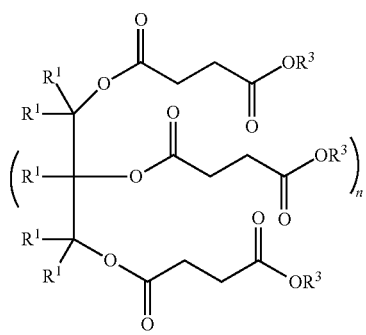

wherein $R^1$, $R^3$ and n are as defined above with respect to formula I.

In some embodiments of formula II, each $R^1$ is H, each $R^3$ is H, and/or n is 1.

In certain embodiments, the compound is trisuccinylglycerol

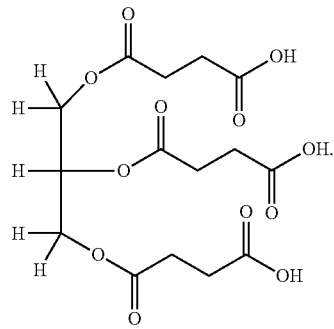 [SMILES: O=C(O)CCC(=O)OCC(COC(=O)CCC(=O)O)OC(=O)CCC(=O)O]

Trisuccinylglycerol is commercially available, for example from Health Chemicals (Jiangsu, China).

The following examples are provided to illustrate certain particular features and/or embodiments. These examples should not be construed to limit the disclosure to the particular features or embodiments described.

EXAMPLES

Example 1: In Vitro Activity Profile of Succinate and its Ability to Correct TCA Cycle Balance in Tissue Culture Cells This example describes experiments to characterize the ability of succinate to correct TCA cycle balance in tissue culture cells from patients with disorders of propionate metabolism. It is believed that PCC deficiency will lead to a deficiency of TCA cycle function in a tissue culture model of PCC deficiency, and that this defect will be corrected through supplementation of succinate.

Methods

Control cells and PCC cells obtained from patients with PA and generated through CRISPR/CAS9 technology are grown in media with and without succinate supplementation and the metabolite profile of cell extracts is determined by metabolomic techniques. First, PCC deficient cells are grown in T-25 flasks in standard DMEM medium with and without supplemental succinate (0.1-2 mmol/L). Cells are harvested, lysed by sonication and intracellular concentrations of TCA cycle intermediates are measured by liquid chromatography-mass spectrometry (LC-MS)/MS. Next, flux through the TCA cycle is measured by incorporation of radiolabel from uniformly labeled $^{14}$C-palmitate into TCA cycle intermediates after incubation with PPC deficient and control cells. PCC deficient cell lines are grown in DMEM complete media and transferred to 6-well plates at a seeding density of ~200,000 cells/well. The media in the wells is changed after 24 hours to DMEM media containing 5% dialyzed fetal bovine serum (FBS). After approximately one hour, the first time point (180 minutes) receives DMEM 5% dialyzed FBS containing universally labeled palmitate with $^{13}$C and $^{15}$N. The cells are incubated at 37° C., 4% $CO_2$ for the following time points: 180 minutes, 60 minutes, 30 minutes, 10 minutes and 0 minutes. The 0 minute time point receives no isotopic labeling. At the end of the incubation, the wells are washed with 75 mM ammonium carbonate for less than 1 minute, and then treated with an extraction buffer (80/20 HPLC-grade MeOH/$H_2O$) in a ratio of 1 μL per 1000 cells/well. The cells are then incubated either on dry ice or in a −80° C. freezer for 10 minutes. The extraction buffer is collected and placed in 1.5 mL Eppendorf tubes, then subjected to centrifugation at 12,000 rpm for 10 minutes at 4° C. The supernatants are then pipetted into a 96-well plate. The 96-well plate contains 3 biological replicates of each time point for both a patient cell line and a control. Incorporation of label into TCA cycle intermediates is measured by LC-MS/MS as below. The experiment is repeated following supplementation with succinate as above.

LC-MS/MS Analysis

The complete LC-MS platform consists of Accela U-HPLC system with quaternary pumps, HTC PAL autosampler (CTC Analytics AG, Zwingen, Switchland), Keystone hot pocket column heater, and EXACTIVE™ ORBITRAP™ mass spectrometer (all from ThermoFisher Scientific, San Jose, CA, unless otherwise noted), controlled by Xcalibur 2.1 software. Liquid chromatography separation is achieved on a Synergy Hydro-RP column (100×2 mm, 2.5 µm particle size, Phenomenex, Torrance, CA) using reversed-phase chromatography with the ion pairing agent tributylamine in the aqueous mobile phase to enhance retention and separation. The present LC method employs a 2.5 µm particle size column. The total run time is 25 minutes. Flow rate is 200 µl/min. Solvent A is 97:3 water:methanol with 10 mM tributylamine and 15 mM acetic acid; solvent B is methanol. The gradient is: 0 minutes, 0% B; 2.5 minutes, 0% B; 5 minutes, 20% B; 7.5 minutes, 20% B; 13 minutes, 55% B; 15.5 minutes, 95% B; 18.5 minutes, 95% B; 19 minutes, 0% B; 25 minutes, 0% B. Other LC parameters are autosampler temperature 4° C., injection volume 10 µl, and column temperature 25° C.

An electrospray ionization interface is used to direct column eluent to the mass spectrometer. Because the ion pairing agent tributylamine causes ion suppression in positive mode, the instrument is operated in negative mode only. Initial instrument optimization (tuning) is done by infusing a mixture of malate (m/z 133.0142), ATP (m/z 505.9885), and coenzyme A (m/z 766.1079), each at 1 µg/ml at a flow rate of 200 µg/ml, using an 11Plus syringe pump (Harvard Apparatus, Boston, MA). Various instrumental settings are optimized to maximize the signal with the final parameters as follows: sheath gas flow rate 25 (arbitrary units), aux gas flow rate 8 (arbitrary units), sweep gas flow rate 3 (arbitrary units), spray voltage 3 kV, capillary temperature 325° C., capillary voltage—50 V, tube lens voltage—100 V. The instrument is mass calibrated using the polytyrosine-1,3,6 standards every three days.

The EXACTIVE™ mass spectrometer has a maximum scan range of m/z 50-4000. For the study of small molecule metabolites, of particular interest is the low mass range (m/z 85-800). In preliminary experiments, it was found that the high amount of phosphate and sulfate in typical cellular media adversely impacted analysis, apparently due to a combination of ion suppression at the ion source and space-charge effects inside the ORBITRAP™ mass spectrometer. To mitigate the latter, during the LC segments at which phosphate ($H_2PO_4-$, m/z 96.9696, ~6 min) and sulfate ($HSO_4-$, m/z 96.9601, ~13 min) elute, a lower scan limit of ≥m/z 100 (rather than m/z 85) was chosen to reduce the accumulation of phosphate and sulfate ions in the ORBITRAP™ mass spectrometer. Although the scan limit does not provide high resolution mass filtration, ions falling outside of the scan range are selected against. Empirically, it was determined that this selection was adequate to improve substantially analytical results. Later in the LC run, the lower m/z limit was raised yet higher, as low molecular weight metabolites elute early in this reversed phase LC method. The final MS scan method is thus made in the following with segments: 0-5 minutes, m/z 85-800; 5-6.7 minutes, m/z 100-800; 6.7-9 minutes, m/z 85-800; 9-16 minutes, m/z 110-1000; 16-24 minutes, m/z 220-1000. The last minute in the LC run is for column equilibrium only and is not scanned. Other MS method settings are, resolution 100,000 at 1 Hz (1 scan per second), AGC (automatic gain control) target 3E6, maximum injection time 100 µS.

Results

It is expected that cell lines from patients with PA or MMA will show a decreased level of TCA cycle intermediates. While all cycle metabolites will be measured initially, the deficit is likely to be adequately demonstrated as a decrease in α-ketoglutarate, glutamate, and glutamine. It is also expected that incorporation of label from palmitate, through the TCA cycle, and into protein will be impaired in deficient cells. Both sets of abnormalities are expected to be reversed by supplementation with succinate.

Example 2: Use of Trisuccinylglycerol (TSG) to Reverse TCA Cycle Deficits In Vivo This example describes experiments to test the efficacy of TSG in ameliorating TCA cycle depletion in mouse models.

Succinate is a TCA cycle intermediate that has been used clinically in the treatment of mitochondrial oxidative phosphorylation deficiencies. While it is suitable for in vitro experiments in cells, it is difficult to deliver pharmacologically relevant doses in patients. A triglycerol form of heptanoate (triheptanoin) has previously been developed that overcomes a similar problem in delivering clinically relevant doses of heptanoate to patients with fatty acid oxidation defects with dramatic effect on their TCA cycle function (Vockley et al., *Mol Genet Metab* 116:53-60, 2015; Roe and Brunengraber *Mol Genet Metab* 116:260-268, 2015). The studies in this example are designed to examine the use of trisuccinylglycerol (TSG) to reverse TCA cycle deficits in propionyl-CoA carboxylase (PCC) and Mut (methylmalonyl-CoA mutase) deficient mice.

Animals receive escalating doses of TSG followed by characterization of their metabolic profile as above. These mice do not live long enough to develop cardiomyopathy, therefore the end points for these studies are metabolic changes. If the therapeutic effect of the TSG is sufficient, a prolongation of life may be observed. In these experiments, deficient animals are treated at birth by daily gavage or IP injection of TSG, and are monitored for prolongation of life to 2 weeks of age. Animals surviving to two weeks of age are sacrificed and blood and tissue levels of TCA cycle intermediates are measured. Other animals are sacrificed immediately prior to expected death and similarly analyzed for TCA cycle intermediates.

It is expected that PA and MMA deficient mice will survive poorly, and that survival will be improved by TSG. While TSG is expected to replete the TCA cycle, it will not reverse the block in propionate metabolism and subsequent acidosis. If TSG is insufficient by itself to significantly alter animal survival, dietary management will be added to the protocol to more closely mimic therapy in humans. Additional studies may include more mildly affected mice (i.e., partial deficiency) if the complete deficiency models cannot be rescued with TSG therapy.

Example 3: Examination of Human Subjects Before and after Treatment with TSG

This example describes a study to examine the status of the TCA cycle in patients with PA and MMA before and after treatment with TSG. It is expected that PA and MMA patients will show deficiency of TCA cycle intermediates before treatment and that these deficits will be reversed by treatment with TSG.

Preliminary toxicity and dosing studies are performed in normal volunteers. A small scale study on five patients with PA and MMA is conducted. Blood and urine samples are examined for TCA cycle intermediates with metabolomics techniques as above. Patients are then treated with once daily dosing of TSG (based on data from the mouse studies in Example 2) for 2 weeks. It is expected that complete repletion of the TCA cycle will occur within 2 weeks. Blood and urine samples are again examined for TCA cycle intermediates with metabolomics techniques as above. A dose escalation study is pursued if TCA cycle intermediates are not increased. These studies are all performed in metabolically stable patients. If the patients show TCA cycle repletion, longer term studies to examine clinical outcome will be performed, as will short term studies on patients in episodes of acute decompensation.

In Western Pennsylvania and Eastern Ohio, there are Amish and Mennonite patients with a mild systemic form of PA that nonetheless has a high incidence of cardiomyopathy. In analogy to long chain fatty acid oxidation disorders, it is hypothesized that the cardiomyopathy in these patients is related to TCA cycle depletion and energy deficiency. It is expected that treatment of these patients with TSG will improve cardiac function. Blood and urine samples are examined with metabolomics techniques before and after treatment. Cardiac echo is used to quantitate cardiac function. Routine plasma measures of cardiomyopathy are obtained including α-troponin, B-type natriuretic peptide (BNP), and creatine phosphokinase (CPK). Specific metabolite concentrations, ratios and profiles are evaluated as biomarkers for the development of cardiomyopathy and/or a marker of treatment. Based on the dosing level established in the above experiments, it is expected that 6 patients with cardiomyopathy will be treated with TSG for 3 months using an open label design. Cardiac parameters are monitored monthly.

It is expected that patients with PA and cardiomyopathy will see dramatic improvement of heart function (likely over 1-3 months). Further studies will include a double blind, placebo, cross over study to demonstrate efficacy. It is also expected that TSG will have clinical benefit in PA and MMA patients without cardiomyopathy.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of restoring tricarboxylic acid (TCA) cycle function in a cell deficient for propionyl-CoA carboxylase (PCC) or methylmalonyl-CoA mutase (MUT), comprising contacting the cell with a compound of formula II

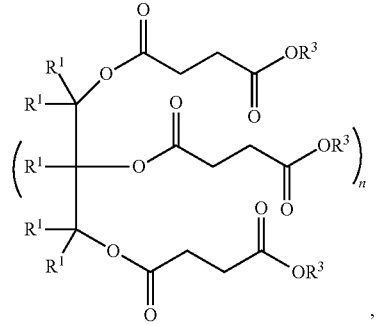

or a pharmaceutically acceptable salt or hydrate thereof,
wherein each $R^1$ independently is H or a $C_{1-6}$alkyl; each $R^3$ independently is a $C_{1-6}$alkyl; and n is 1;
wherein the compound of formula II is the only therapeutic agent used in the method.

2. The method of claim 1, wherein the method is an in vitro method.

3. The method of claim 1, wherein the method is an in vivo method comprising administering the compound to a subject with a PCC or MUT deficiency.

4. The method of claim 3, wherein the compound is administered to the subject once per day.

5. The method of claim 3, wherein the compound is administered in multiple divided doses.

6. The method of claim 3, wherein the compound is administered orally or intravenously.

7. The method of claim 3, wherein each $R^1$ independently is hydrogen, methyl, ethyl, n-propyl, isopropyl, n-butyl, isobutyl, sec-butyl, t-butyl, n-pentyl or neopentyl.

8. The method of claim 3, wherein each $R^3$ independently is methyl, ethyl, n-propyl, isopropyl, n-butyl, isobutyl, sec-butyl, t-butyl, n-pentyl or neopentyl.

9. The method of claim 1, wherein each $R^1$ independently is hydrogen, methyl, ethyl, n-propyl, isopropyl, n-butyl, isobutyl, sec-butyl, t-butyl, n-pentyl or neopentyl.

10. The method of claim 1, wherein each $R^3$ independently is methyl, ethyl, n-propyl, isopropyl, n-butyl, isobutyl, sec-butyl, t-butyl, n-pentyl or neopentyl.

* * * * *